(12) United States Patent
Henriksen et al.

(10) Patent No.: US 7,597,877 B2
(45) Date of Patent: Oct. 6, 2009

(54) ADMINISTERING A GRAVITY SEGREGATION DISPERSION BY CONTINUOUS INFUSION

(75) Inventors: Ingrid Henriksen, Oslo (NO); Tore Omtveit, Eiksmarka (NO); Vera Kasparkova, Oslo (NO); Anne Kjersti Fahlvik, Oslo (NO)

(73) Assignee: GE Healthcare AS, Oslo (NO)

( * ) Notice: Subject to any disclaimer, the term of this patent is extended or adjusted under 35 U.S.C. 154(b) by 482 days.

(21) Appl. No.: 10/071,505

(22) Filed: Feb. 8, 2002

(65) Prior Publication Data

US 2002/0197211 A1    Dec. 26, 2002

Related U.S. Application Data

(63) Continuation of application No. PCT/GB00/03310, filed on Aug. 25, 2000.

(30) Foreign Application Priority Data

Aug. 27, 1999    (GB)    .................................. 9920392.9

(51) Int. Cl.
*A61B 8/00* (2006.01)
*A61K 9/127* (2006.01)

(52) U.S. Cl. ...................................... 424/9.52; 424/450

(58) Field of Classification Search ......... 424/9.5–9.52, 424/450; 604/80, 82
See application file for complete search history.

(56) References Cited

U.S. PATENT DOCUMENTS

| 4,572,203 | A | | 2/1986 | Feinstein |
| 5,242,392 | A | * | 9/1993 | Vaughn ........................ 604/80 |
| 5,897,851 | A | | 4/1999 | Quay et al. |
| 6,033,645 | A | * | 3/2000 | Unger et al. .................. 424/9.5 |

FOREIGN PATENT DOCUMENTS

| WO | WO97/48337 A | 12/1997 |
| WO | WO98/18501 A | 5/1998 |
| WO | WO99/32034 A | 7/1999 |

OTHER PUBLICATIONS

Remington, The Science and Practice of Pharmacy 19$^{th}$ ed., pp. 1551-1554, 1995, Mack Publishing Company (Remington).*

* cited by examiner

*Primary Examiner*—Yong S Chong
(74) *Attorney, Agent, or Firm*—Craig Bohlken

(57) ABSTRACT

Method and apparatus for continuous infusion to a subject of dispersions in which the dispersed phase is susceptible to flotation or sedimentation. The dispersion is controllably delivered from an upper or lower extremity of an essentially vertically positioned delivery vessel, e.g. syringe 2, and is then admixed with flushing medium, e.g. from infusion minibag 8, prior to administration to the subject. Vertical positioning of the delivery device maximises the distance through which flotation or sedimentation may occur, thereby substantially reducing the effects of separation over a given period of time compared to use of a corresponding horizontal delivery vessel such as a syringe placed in a conventional syringe driver.

8 Claims, 3 Drawing Sheets

ADMINISTERING A GRAVITY SEGREGATION DISPERSION BY CONTINUOUS INFUSION

This application is a continuation application of international application number PCT/GB00/03310 filed Aug. 25, 2000, the entire disclosure of which is hereby incorporated by reference.

BACKGROUND OF THE INVENTION

This invention relates to the administration of dynamic (i.e. gravity segregating) particulate dispersion systems, e.g. gas-containing diagnostic contrast agents, more particularly to apparatus and a method for the controlled and substantially steady state administration of such dispersions by infusion.

In the field of ultrasonography it is well known that contrast agents comprising dispersions of gas microbubbles are particularly efficient backscatterers of ultrasound by virtue of the low density and ease of compressibility of the microbubbles. Such microbubble dispersions, if appropriately stabilised, may permit highly effective ultrasound visualisation of, for example, the vascular system and tissue microvasculature, often at advantageously low doses of the contrast agent.

Gas-containing contrast media are also known to be effective in magnetic resonance (MR) imaging, e.g. as susceptibility contrast agents which will act to reduce MR signal intensity. Oxygen-containing contrast media also represent potentially useful paramagnetic MR contrast agents.

In the field of X-ray imaging gases such as carbon dioxide may be used as intravascular contrast agents. Moreover, the use of radioactive gases, e.g. radioactive isotopes of inert gases such as xenon, has been proposed in scintigraphy, for example for blood pool imaging.

Gas-containing ultrasound contrast agents are usually administered intravenously as a single or multiple bolus dosage, leading to a rapid and pronounced but relatively short lived rise in backscatter intensity in respect of blood-perfused tissue and organs as the bolus mixes with surrounding blood and is carried through the circulation system. A plot of backscatter intensity against time therefore shows a relatively narrow and high signal intensity peak; backscatter measurements are normally made during the existence of this peak, although this may give rise to problems in, for example, the imaging of deeper tissue and organs where high backscatter from overlying tissue may cause excessive shadowing during the peak period.

As discussed in WO-A-9748337, diagnostic artefacts such as shadowing may be reduced by controlling the rate of administration of the contrast agent and/or by administering a flush such as normal saline after administration of the contrast agent. Contrast agent administration rates of $1\text{-}8\times10^{6}$ vesicles/kg-sec or $1\times10^{-7}$ to $3\times10^{-3}$ cc gas/kg-sec and flush rates of 0.01-2.4 ml/sec are suggested; the contrast agent is typically administered over a period of 5-20 seconds, and any subsequent flush is typically administered over a period in the range 10 seconds to 10 minutes.

Continuous infusion of ultrasound contrast agents, for example over a period in the range from one minute to one hour, is of potential interest in that it may permit administration of the contrast agent at a rate which minimises diagnostic artefacts such as shadowing and may lengthen the useful time window for imaging beyond the relatively short duration of the backscatter signal peak resulting from passage of a contrast agent bolus.

Thus, for example, Albrecht et al. in Radiology 207, pp. 339-347 (1998) note that the use of continuous contrast agent infusion to provide prolonged enhancement of Doppler signals is advantageous in that it may permit completion of lengthy imaging procedures such as studies of the renal arteries or peripheral leg veins and may optimise dose effectiveness of the contrast agents, as well as reducing saturation artefacts.

Administration of contrast agents by infusion may also be useful in procedures based on imaging of contrast agent in the recirculating phase following admixture with the blood pool, as described in WO-A-9908714.

A problem with the continuous infusion of gas-containing diagnostic contrast agents arises from the tendency of gas-containing components such as microbubbles to float, since this will lead to inhomogeneities forming within vessels such as power-driven syringes which may be used to administer the contrast agent. This may, for example, lead to an increase in microbubble concentration in the upper part of such a vessel and/or to changes in size distribution occurring at various points within the vessel as larger microbubbles float more rapidly than smaller microbubbles.

A possible solution to this problem is proposed in WO-A-9927981, which discloses powered injector systems comprising a syringe which is subjected to rotational or rocking motion in order to maintain homogeneity within the contents thereof. In specific embodiments the barrel of the syringe is positioned horizontally in contact with wheels or moveable brackets which are capable of alternately rotating the syringe in opposite directions about its longitudinal (i.e. horizontal) axis.

It will be appreciated that the incorporation of such rotational or other agitational means into syringe driver apparatus necessarily complicates the design and significantly increases the cost of such apparatus, so that there is an ongoing need for apparatus which permits the continuous infusion of gas-containing ultrasound contrast agents or other gravity segregating dispersions while maintaining substantial homogeneity of the contrast agent or other dispersion.

SUMMARY OF INVENTION

The present invention is based on the finding that controlled delivery of a substantially homogeneous gravity segregating dispersion may be achieved by an infusion procedure in which the dispersion is delivered from an upper or lower extremity of an essentially vertically positioned delivery vessel, e.g. a syringe, tubing or other cylindrically shaped reservoir, and is admixed with a flushing medium prior to administration to a subject.

By using an essentially vertically positioned cylindrical delivery vessel such as a syringe, as opposed to the horizontal orientation normally employed in delivery devices such as syringe drivers, the height of the dispersion sample in the vessel is greatly increased, thereby extending the distance through which gravity segregation may occur. Since relatively low density dispersed moieties such as microbubbles or other gas-containing components of a given size will rise through carrier liquid at a constant rate, this significantly reduces the effects of flotation separation and thereby improves dose control over a given period of time. Similar considerations apply to dispersions of relatively high density microparticles, emulsion droplets etc. which tend to sediment over time.

Co-administration of the dispersion with an admixed flushing medium further enhances product homogeneity, e.g. by reducing the residence time of the dispersion in connecting tubing etc., thereby reducing its susceptibility to gravity segregation. Admixture with flushing medium also permits particularly efficient control of administration of the dispersion since the flow rates of both the dispersion and the flushing medium may be independently controlled.

Admixture of the dispersion with flushing medium almost immediately prior to administration to a subject is particularly advantageous in the administration of dispersions such as gas microbubble-containing contrast agents, which often show instability if stored in diluted form, e.g. if diluted prior to transfer into a syringe or other delivery vessel.

Moreover, where administration is by intravascular (e.g. intravenous) injection, coadministration of admixed flushing medium at a single injection site assists in maintenance of an open injection route independent of dispersion flow and local blood flow variations.

BRIEF DESCRIPTION ON THE FIGURES

Figure 1:
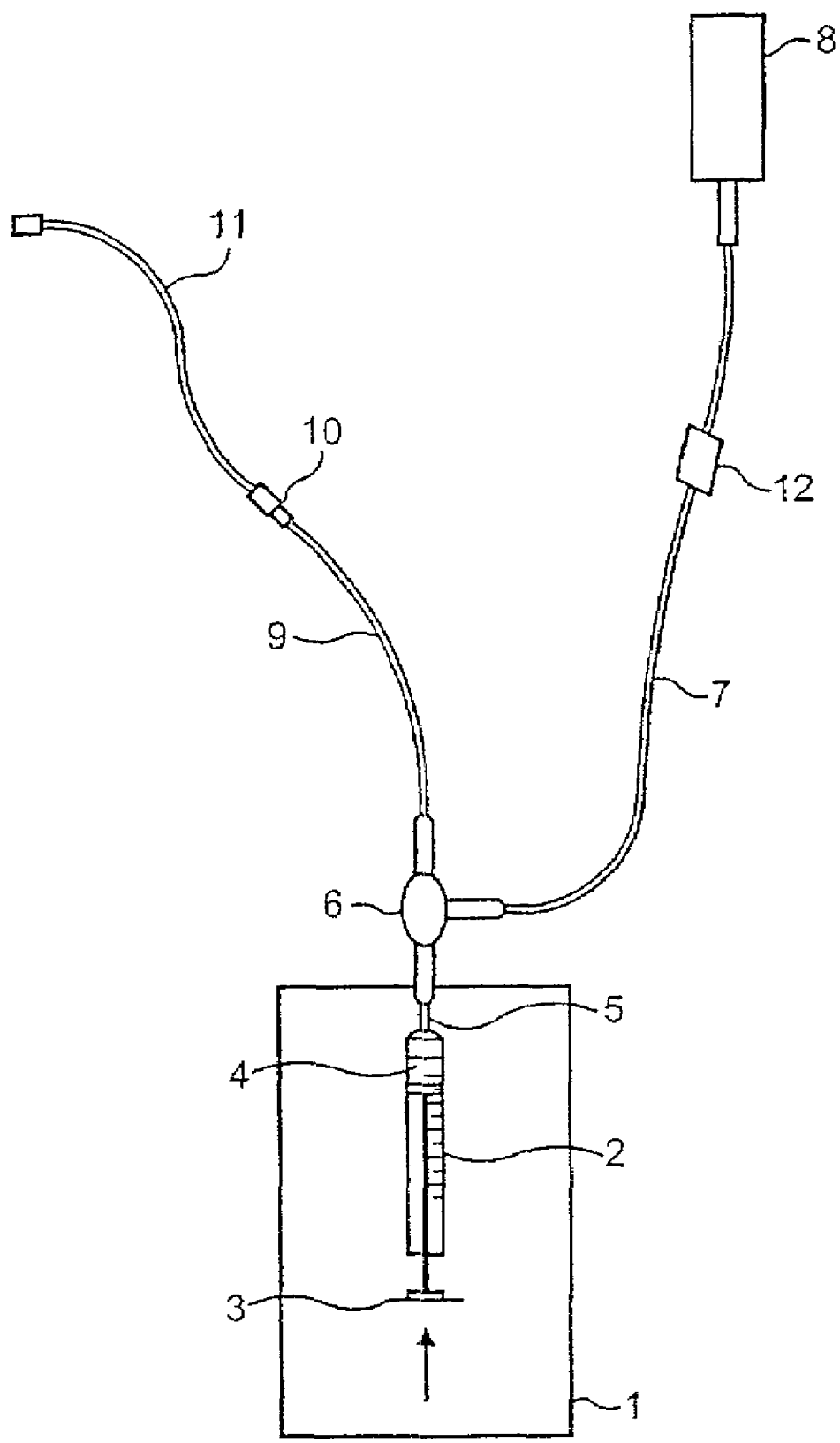
Figure 2:
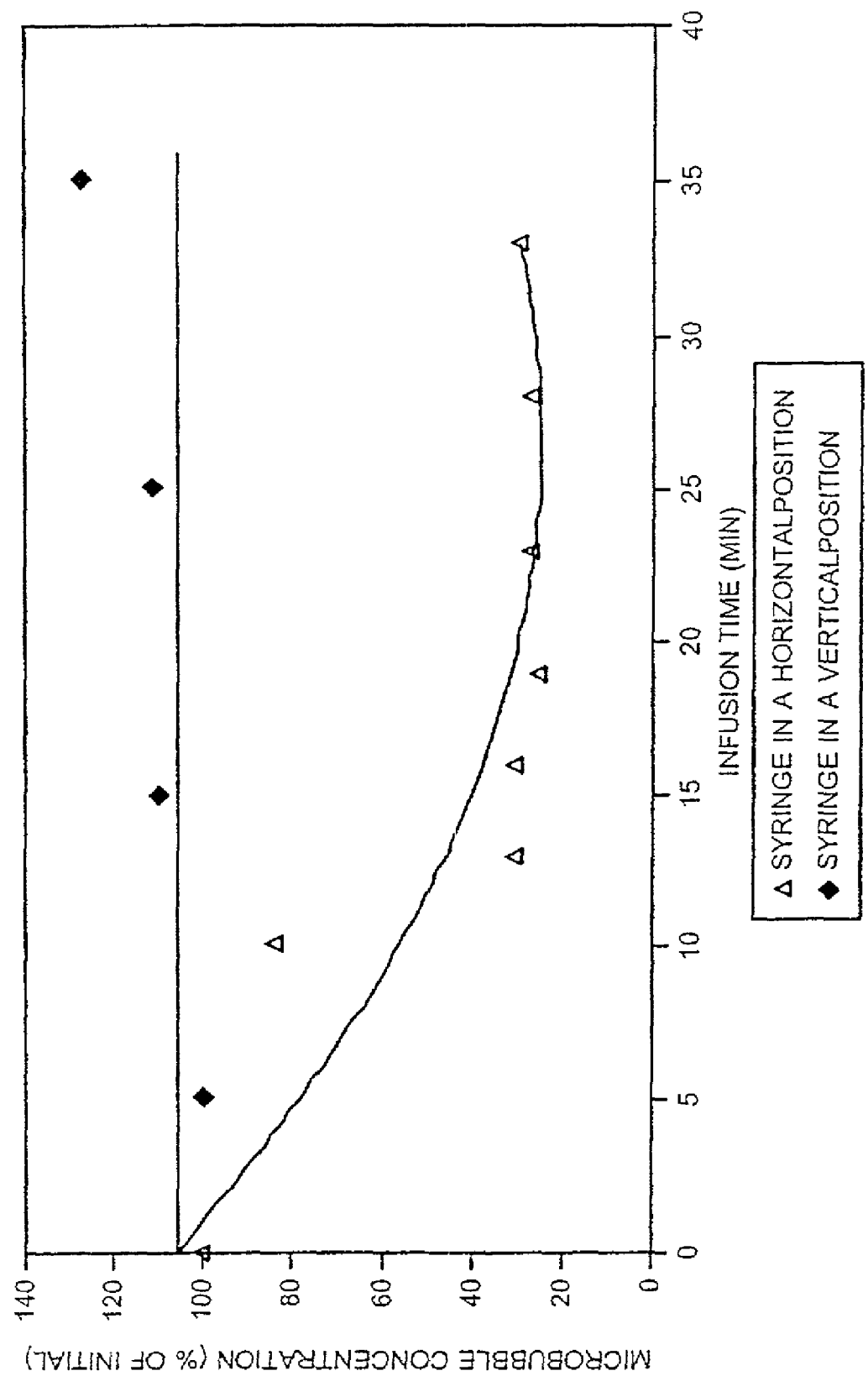
Figure 3:
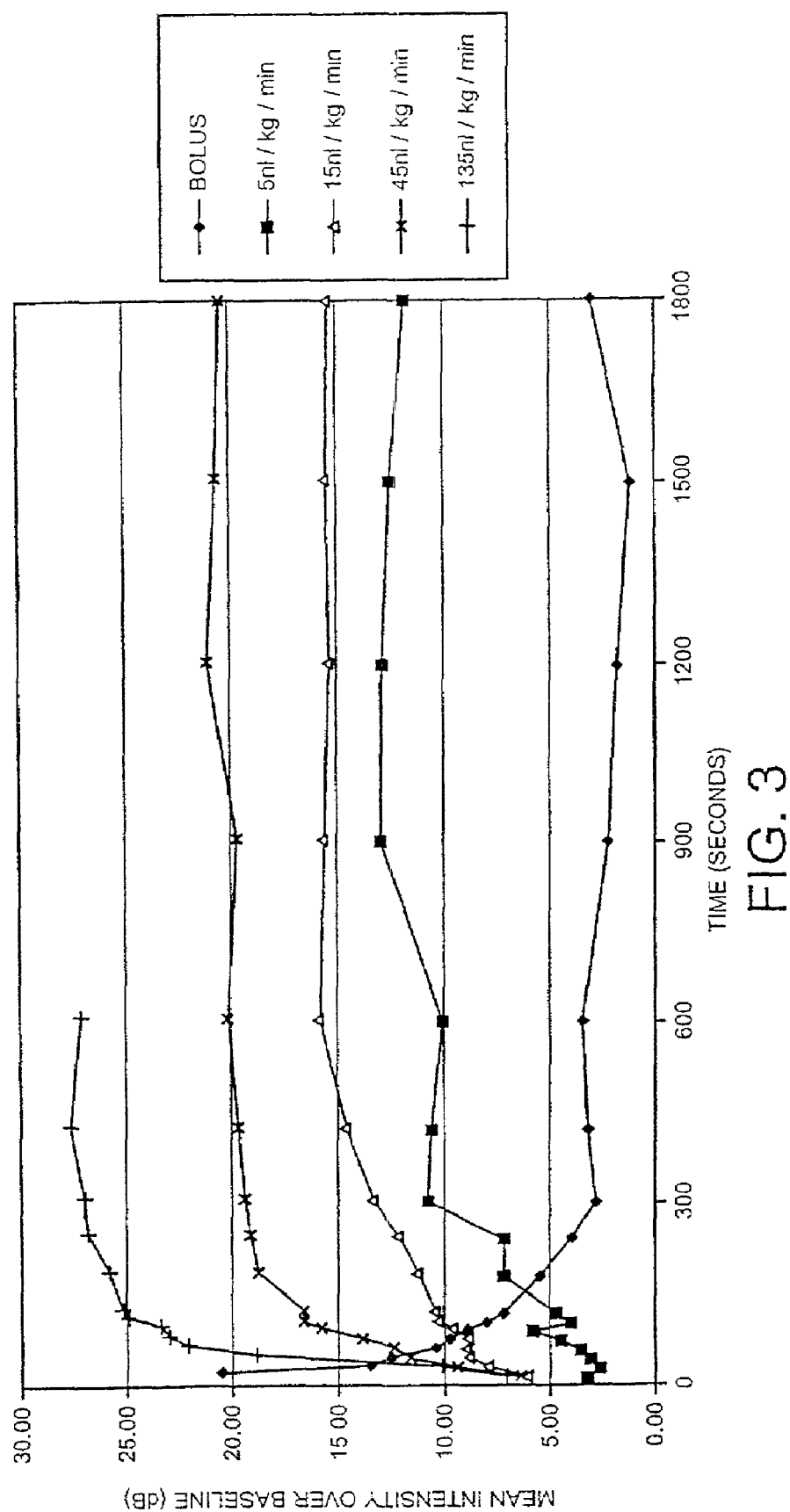

In the accompanying figures:

FIG. 1 is a schematic representation of one embodiment of apparatus useful in accordance with the invention;

FIG. 2 comprises plots of microbubble concentration against infusion time for the in vitro test system described in Example 6 hereinafter and for a comparative study using a horizontally positioned syringe; and FIG. 3 comprises plots of echogenicity against time obtained in accordance with the in vivo studies described in Example 15 hereinafter.

Referring to FIG. 1 in more detail, syringe driver 1 (detail not shown) is adapted to receive vertically positioned syringe 2 and controllably to drive syringe plunger 3 in an upward direction so as to expel dispersion 4 through delivery outlet 5 at the upper extremity of the syringe. Three way stopcock 6 connects outlet 5 and feed 7 from saline infusion minibag 8 to conduit tube 9 which is connected via Luer lock 10 to infusion feed line 11, which in turn is connectable to an injection needle or catheter (not shown). The flow rate of dispersion is controllable by adjusting syringe driver 1. The flow rate of saline from minibag 8 is controllable by adjusting one or more of stopcock 6, valve 12 and the height of the minibag.

The following non-limitative examples serve to illustrate the invention.

DETAILED DESCRIPTION OF THE INVENTION

Thus according to one aspect of the present invention there is provided a method of administering a gravity segregating dispersion, e.g. a gas-containing contrast agent, to a subject by continuous infusion, wherein said dispersion is controllably delivered from an upper or lower extremity of an essentially vertically positioned delivery vessel, e.g. a syringe, and thereafter is admixed with a flushing medium prior to administration to the subject.

According to a further aspect the invention provides apparatus useful in the administration of a gravity segregating dispersion, e.g. a gas-containing contrast agent, by continuous infusion, said apparatus comprising (i) a delivery device adapted to retain a dispersion-containing delivery vessel in an essentially vertical position and controllably to expel dispersion from an upper or lower extremity of said vessel; (ii) mixing means adapted to effect admixture of said expelled dispersion with a flushing medium; and (iii) conduit means adapted to conduct said admixed dispersion and flushing medium to an administration device.

The term "essentially vertical" as used herein denotes that the longitudinal axis of the delivery vessel should be positioned within about 30E of vertical, preferably within 15E and more preferably within 5E of vertical. The vessel may be positioned for delivery of dispersion from either its upper or lower extremity, i.e. for upward or downward delivery respectively.

In the case of dispersions comprising a relatively low density dispersed phase, such flotation as may occur during administration of the dispersion will tend to lead to a reduction in dispersed phase concentration as administration proceeds in the case where the delivery vessel is positioned for upward delivery and to a corresponding increase in concentration in the case where the delivery vessel is positioned for downward delivery. It will be appreciated that the converse will apply for dispersions comprising a relatively high density dispersed phase which is susceptible to sedimentation. Such concentration changes may, if desired, be counteracted by appropriate adjustment of the rates at which the dispersion and flushing medium are coadministered. Additionally or alternatively the delivery vessel may be inverted at a suitable stage during infusion.

It is preferred that the delivery vessel is positioned so that the bulk flow direction of dispersion during expulsion is the same as the direction of segregation of the dispersed phase, since this will assist in counteracting the formation of concentration gradients of dispersed phase within the dispersion during administration. Thus, for example, in the case of dispersions such as gas-containing contrast agents in which the dispersed phase is susceptible to flotation, it is preferred to use delivery vessels positioned for upward delivery.

Delivery devices which may be used in apparatus according to the invention include syringe driver means such as power injection systems in which the syringe plunger is controllably driven by an appropriate automated mechanism, for example an electrically powered and controlled helical screw or push rod.

Where the infused dispersion is a gas-containing contrast agent it may, for example, be administered at a rate in the range 0.001-0.5 ml/minute, preferably 0.01-0.25 ml/minute, and may be selected to take account of factors such as the gas concentration and, in the case of ultrasound studies, the desired degree of attenuation. The infusion rate will depend on the body weight of the subject, and will typically be about 0.06:kg/hour. Such contrast agents may, for example, be administered over an infusion period of up to one hour, typically for a period of 15-20 minutes; steady state distribution of contrast agent in vivo will typically be achieved after 1-2 minutes The flushing medium may be any appropriate biocompatible liquid, but is preferably normal (i.e. 0.9%) saline. It may, for example, be administered by gravitational flow using appropriate flow rate controlling means, or may be delivered using a controllable pump. Flow rates of 0.5-2 ml/minute, have been found to be appropriate although higher flow rates, e.g. up to 5 ml/minute, may also be useful.

Mixing of the dispersion and flushing medium may, for example, be effected in a three way connector, e.g. a T-piece, a Y-piece or a tap such as a three way stopcock, which is also connected via appropriate tubing to an administration device, e.g. an injection device such as a needle or catheter. It is preferred that connections are kept to a minimum and are made using low volume tubing in order to minimise transit time of the dispersion and thus to minimise the potential for segregation of the dispersed phase.

Gases which may be present in gas-containing contrast agents administered in accordance with the invention include any biocompatible substances, including mixtures, which are at least partially, e.g. substantially or completely, in gaseous or vapour form at the normal human body temperature of 37

EC. Representative gases thus include air; nitrogen; oxygen; carbon dioxide; hydrogen; inert gases such as helium, argon, xenon or krypton; sulphur fluorides such as sulphur hexafluoride, disulphur decafluoride or trifluoromethylsulphur pentafluoride; selenium hexafluoride; optionally halogenated silanes such as methylsilane or dimethylsilane; low molecular weight hydrocarbons (e.g. containing up to 7 carbon atoms), for example alkanes such as methane, ethane, a propane, a butane or a pentane, cycloalkanes such as cyclopropane, cyclobutane or cyclopentane, alkenes such as ethylene, propene, propadiene or a butene, and alkynes such as acetylene or propyne; ethers such as dimethyl ether; ketones; esters; halogenated low molecular weight hydrocarbons (e.g. containing up to 7 carbon atoms); and mixtures of any of the foregoing. Advantageously at least some of the halogen atoms in halogenated gases are fluorine atoms; thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethylfluoride, 1,1-difluoroethane and perfluorocarbons. Representative perfluorocarbons include perfluoroalkanes such as perfluoromethane, perfluoroethane, perfluoropropanes, perfluorobutanes (e.g. perfluoro-n-butane, optionally in admixture with other isomers such as perfluoro-iso-butane), perfluoropentanes, perfluorohexanes or perfluoroheptanes; perfluoroalkenes such as perfluoropropene, perfluorobutenes (e.g. perfluorobut-2-ene), perfluorobutadiene, perfluoropentenes (e.g. perfluoropent-1-ene) or perfluoro-4-methylpent-2-ene; perfluoroalkynes such as perfluorobut-2-yne; and perfluorocycloalkanes such as perfluorocyclobutane, perfluoromethylcyclobutane, perfluorodimethylcyclobutanes, perfluorotrimethyl-cyclobutanes, perfluorocyclopentane, perfluoromethyl-cyclopentane, perfluorodimethylcyclopentanes, perfluorocyclohexane, perfluoromethylcyclohexane or perfluorocycloheptane. Other halogenated gases include methyl chloride, fluorinated (e.g. perfluorinated) ketones such as perfluoroacetone and fluorinated (e.g. perfluorinated) ethers such as perfluorodiethyl ether. The use of perfluorinated gases, for example sulphur hexafluoride and perfluorocarbons such as perfluoropropane, perfluorobutanes, perfluoropentanes and perfluorohexanes, may be particularly advantageous in view of the recognised high stability in the blood stream of microbubbles containing such gases. Other gases with physicochemical characteristics which cause them to form highly stable microbubbles in the blood stream may likewise be useful.

Representative examples of contrast agent formulations include microbubbles of gas stabilised (e.g. at least partially encapsulated) by a coalescence-resistant surface membrane (for example gelatin, e.g. as described in WO-A-8002365), a filmogenic protein (for example an albumin such as human serum albumin, e.g. as described in U.S. Pat. Nos. 4,718,433, 4,774,958, 4,844,882, EP-A-0359246, WO-A-9112823, WO-A-9205806, WO-A-9217213, WO-A-9406477, WO-A-9501187 or WO-A-9638180), a polymer material (for example a synthetic biodegradable polymer as described in EP-A-0398935, an elastic interfacial synthetic polymer membrane as described in EP-A-0458745, a microparticulate biodegradable polyaldehyde as described in EP-A-0441468, a microparticulate N-dicarboxylic acid derivative of a polyamino acid - polycyclic imide as described in EP-A-0458079, or a biodegradable polymer as described in WO-A-9317718 or WO-A-9607434), a non-polymeric and non-polymerisable wall-forming material (for example as described in WO-A-9521631), or a surfactant (for example a polyoxyethylene-polyoxypropylene block copolymer surfactant such as a Pluronic, a polymer surfactant as described in WO-A-9506518, or a film-forming surfactant such as a phospholipid, e.g. as described in WO-A-9211873, WO-A-9217212, WO-A-9222247, WO-A-9409829, WO-A-9428780, WO-A-9503835 or WO-A-9729783). Contrast agent formulations comprising free microbubbles of selected gases, e.g. as described in WO-A-9305819, or comprising a liquid-in-liquid emulsion in which the boiling point of the dispersed phase is below the body temperature of the subject to be imaged, e.g. as described in WO-A-9416739, may also be used.

Other useful gas-containing contrast agent formulations include gas-containing solid systems, for example microparticles (especially aggregates of microparticles) having gas contained therewithin or otherwise associated therewith (for example being adsorbed on the surface thereof and/or contained within voids, cavities or pores therein, e.g. as described in EP-A-0122624, EP-A-0123235, EP-A-0365467, WO-A-9221382, WO-A-9300930, WO-A-9313802, WO-A-9313808 or WO-A-9313809). It will be appreciated that the echogenicity of such microparticulate contrast agents may derive directly from the contained/associated gas and/or from gas (e.g. microbubbles) liberated from the solid material (e.g. upon dissolution of the microparticulate structure). The invention may also be useful in conjunction with contrast agent systems based on microspheres comprising a therapeutic compound as described in e.g. WO-A-9851284 and WO-A-9927981.

The disclosures of all of the above-described documents relating to gas-containing contrast agent formulations are incorporated herein by reference.

Gas microbubbles and other gas-containing materials such as microparticles preferably have an initial average size not exceeding 10 :m (e.g. of 7 :m or less) in order to permit their free passage through the pulmonary system following administration, e.g. by intravenous injection. However, larger microbubbles may be employed where, for example, these contain a mixture of one or more relatively blood-soluble or otherwise diffusible gases such as air, oxygen, nitrogen or carbon dioxide with one or more substantially insoluble and non-diffusible gases such as perfluorocarbons. Outward diffusion of the soluble/diffusible gas content following administration will cause such microbubbles rapidly to shrink to a size which will be determined by the amount of insoluble/non-diffusible gas present and which may be selected to permit passage of the resulting microbubbles through the lung capillaries of the pulmonary system.

Where phospholipid-containing contrast agent formulations are employed in accordance with the invention, e.g. in the form of phospholipid-stabilised gas microbubbles, representative examples of useful phospholipids include lecithins (i.e. phosphatidylcholines), for example natural lecithins such as egg yolk lecithin or soya bean lecithin, semisynthetic (e.g. partially or fully hydrogenated) lecithins and synthetic lecithins such as dimyristoylphosphatidylcholine, dipalmitoylphosphatidylcholine or distearoylphosphatidylcholine; phosphatidic acids; phosphatidylethanolamines; phosphatidylserines; phosphatidylglycerols; phosphatidylinositols; cardiolipins; sphingomyelins; fluorinated analogues of any of the foregoing; mixtures of any of the foregoing and mixtures with other lipids such as cholesterol. The use of phospholipids predominantly (e.g. at least 75%) comprising molecules individually bearing net overall charge, e.g. negative charge, for example as in naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and/or cardiolipins, for example as described in WO-A-9729783, may be particularly advantageous.

Representative examples of materials useful in gas-containing contrast agent microparticles include carbohydrates (for example hexoses such as glucose, fructose or galactose; disaccharides such as sucrose, lactose or maltose; pentoses such as arabinose, xylose or ribose; "-, $- and (-cyclodextrins; polysaccharides such as starch, hydroxyethyl starch, amylose, amylopectin, glycogen, inulin, pulullan, dextran, carboxymethyl dextran, dextran phosphate, ketodextran, aminoethyldextran, alginates, chitin, chitosan, hyaluronic acid or heparin; and sugar alcohols, including alditols such as mannitol or sorbitol), inorganic salts (e.g. sodium chloride), organic salts (e.g. sodium citrate, sodium acetate or sodium tartrate), X-ray contrast agents (e.g. any of the commercially available carboxylic acid and non-ionic amide contrast agents typically containing at least one 2,4,6-triiodophenyl group having substituents such as carboxyl, carbamoyl, N-alkylcarbamoyl, N-hydroxyalkylcarbamoyl, acylamino, N-alkylacylamino or acylaminomethyl at the 3- and/or 5-positions, as in metrizoic acid, diatrizoic acid, iothalamic acid, ioxaglic acid, iohexol, iopentol, iopamidol, iodixanol, iopromide, metrizamide, iodipamicle, meglumine iodipamide, meglumine acetrizoate and meglumine diatrizoate), polypeptides and proteins (e.g. gelatin or albumin such as human serum albumin), and mixtures of any of the foregoing.

The method and apparatus of the invention may be particularly useful for infusion of the ultrasound contrast agents known as Levovist, Albunex, Optison, Definity, Imagent, Sonovue, Echogen, Sonogen and Sonazoid.

The method and apparatus of the invention may also be useful in sequential imaging procedures, for example in which a patient undergoes a first period of contrast agent infusion and imaging, is then subjected to stress (e.g. through exercise or by administration of a pharmacological stress agent such as adenosine, dobutamine, dipyridamole or arbutamine) and undergoes a second period of contrast agent infusion and imaging during or after this subjection to stress.

EXAMPLES

The following examples illustrate certain preferred embodiments of the instant invention but are not intended to be illustrative of all embodiments.

Preparation 1—Hydrogenated Phosphatidylserine-encapsulated Perfluorobutane Microbubbles Hydrogenated phosphatidylserine (5 mg/ml in a 1% w/w solution of propylene glycol in purified water) and perfluorobutane gas were homogenised in-line at 7800 rpm and ca. 40EC to yield a creamy-white microbubble dispersion. The dispersion was fractionated to substantially remove under-sized microbubbles (C2 :m) and the volume of the dispersion was adjusted to the desired microbubble concentration. Sucrose was then added to a concentration of 92 mg/ml. 2 ml portions of the resulting dispersion were filled into 10 ml flat-bottomed vials specially designed for lyophilisation, and the contents were lyophilised to give a white porous cake. The lyophilisation chamber was then filled with perfluorobutane and the vials were sealed. Unless otherwise stated, 2 ml of water were added to a lyophilised product-containing vial prior to use and the contents were hand-shaken for several seconds, giving a perfluorobutane microbubble dispersion with a concentration range of $5\text{-}20\times10^8$ microbubbles/ml (7-13 :l/ml).

Examples 1-6

In vitro Studies

The contents of vials prepared as in Preparation 1 were mixed with water (5 ml) from a syringe and gently hand shaken to give perfluorobutane microbubble dispersions with a microbubble concentration of about 3 :l/ml (Examples 1 to 5). In the procedure of Example 6 the contents of three vials were each mixed with 2 ml of water and the resulting dispersions were then pooled. Each of the thus-obtained microbubble dispersions was drawn into a syringe, which was vertically positioned in a module DPC syringe pump and connected to a low volume extension tube equipped with a 3 way stopcock and an administration set for delivery of normal saline from an infusion minibag, as shown in FIG. 1 The syringe pump rate and the saline rate were varied as shown in Table 1, which also records the calculated and observed microbubble concentrations and the observed periods over which steady state infusion was maintained (measured as timings from the start of infusion).

TABLE 1

| Example No. | Syringe pump rate (ml/min) | Saline flow rate (ml/min) | Calculated microbubble conc. (:1/ml) | Observed microbubble conc. (:1/ml) | Period of steady state infusion (min) |
|---|---|---|---|---|---|
| 1 | 0.017 | 1 | 0.05 | 0.11" 0.04 | 10-60 |
| 2 | 0.1 | 1 | 0.3 | 0.29" 0.05 | 5-30 |
| 3 | 0.2 | 1 | 0.6 | 0.57" 0.06 | 5-16 |
| 4 | 0.017 | 2 | 0.025 | 0.08" 0.01 | 10-60 |
| 5 | 0.1 | 2 | 0.15 | 0.17" 0.03 | 5-30 |
| 6 | 0.1 | 2 | 0.35 | 0.44" 0.04 | 5-35 |

FIG. 2 shows a plot of microbubble concentration (expressed as percentage of initial concentration) against time as determined in the procedure of Example 6. For comparison, the variation of microbubble concentration with time determined using an equivalent procedure with a horizontally positioned syringe is also shown. It can readily be seen that in the procedure according to the invention a substantially steady microbubble concentration is maintained, whereas in the comparative test the microbubble concentration rapidly decreases as infusion proceeds.

It will be appreciated that the length of the administration window will be shortened at higher syringe pump rates given the fixed volume of contrast agent present in a syringe.

Examples 7-14

In vitro Studies

In order to demonstrate the possibility of adjusting microbubble dose for different infusion procedures, a study was conducted according to the general procedure of Example 6 above, using a saline infusion rate of 2 ml/minute while varying the syringe pump rate as shown in Table 2, which also records the calculated and observed microbubble concentrations.

TABLE 2

| Example No. | Infusion time (min) | Syringe pump rate (ml/min) | Calculated microbubble conc. (:1/ml) | Observed microbubble conc. (:1/ml) |
|---|---|---|---|---|
| 7  | 5  | 0.1  | 0.15  | 0.20 |
| 8  | 10 | 0.05 | 0.075 | 0.10 |
| 9  | 15 | 0.05 | 0.075 | 0.12 |
| 10 | 20 | 0.12 | 0.18  | 0.20 |
| 11 | 25 | 0.12 | 0.18  | 0.19 |
| 12 | 30 | 0.05 | 0.075 | 0.08 |
| 13 | 35 | 0.05 | 0.075 | 0.09 |
| 14 | 40 | 0.05 | 0.075 | 0.07 |

Example 15

In vivo Study

Second harmonic imaging of the anterior myocardium was performed on an open chest model in 6 dogs (15-25kg, both sexes) using an ATL HDI 3000 scanner with a mechanical index of 0.6 and 1:4 triggering. Images were recorded following injection of a bolus of contrast agent prepared as in Preparation 1 at a concentration of 30 nl perfluorobutane/kg, and during infusion of contrast agent in accordance with the method of the invention at rates corresponding to 5, 15, 45 and 135 nl perfluorobutane/kg/min. The contrast effects in the region of interest are shown in FIG. 3.

Example 16

A microbubble suspension is prepared as in Example 1 of WO-A-9748337 and administered according to the method of the invention.

Example 17

The commercially available ultrasound product sold under the trade name Optison is administered according to the method of the invention.

Example 18

Contrast agents are prepared as in Example 2 of WO-A-9927981 and administered according to the method of the invention.

Example 19

Triggered ultraharmonic cardiac imaging of a patient with normal cardiac arteries was performed with triggering at every heart beat, every second heart beat, every fourth heart beat and every eighth heart beat. The heart was imaged from apical 2-chamber and 4-chamber views during dipyridamole-induced stress. Contrast agent prepared as in Preparation 1 was infused at a rate of 10 :1/kg/minute throughout the entire imaging period.

Increased videodensity was observed in each of the myocardial segments (the myocardium was divided into 16 segments according to the definitions of the American Society of Echocardiography) for each of the triggering intervals. The increase in intensity ranged from 8 to 10 dB in the different myocardial segments for the highest triggering interval (8 heart beats).

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A method of administering a gas-containing contrast agent to a subject by continuous infusion, the improvement comprising enhancing product homogeneity by controllably delivering said gas-containing contrast agent from an upper extremity of an essentially vertically positioned syringe and admixing with a flushing medium prior to administration to the subject, delivering the admixed product to the subject over an infusion period of 5-60 minutes.

2. The method of claim 1 wherein delivery of said gas-containing contrast agent from said syringe is controlled by a syringe driver.

3. The method of claim 1 wherein said gas comprises sulphur hexafluoride or a perfluorinated low molecular weight hydrocarbon.

4. The method of claim 3 wherein said perfluorinated hydrocarbon is perfluoropropane or perfluorobutane.

5. The method of claim 1 wherein said gas is present as albumin-stabilised microbubbles.

6. The method of claim 1 wherein said flushing medium is normal saline.

7. The method of claim 1 wherein the admixed gas-containing contrast agent and flushing medium are administered by injection.

8. The method of claim 1 wherein the flushing medium is administered at a flow rate of 0.5-5 ml/minute.

* * * * *